United States Patent
McGrath et al.

(10) Patent No.: US 6,537,523 B1
(45) Date of Patent: *Mar. 25, 2003

(54) DIAGNOSIS AND TREATMENT OF CANCER HAVING CLONAL MACROPHAGE INVOLVEMENT

(75) Inventors: Michael S. McGrath, Burlingame, CA (US); Brian Herndier, San Francisco, CA (US); Bruce Shiramizu, Pacifica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/975,532

(22) Filed: Nov. 20, 1997

Related U.S. Application Data

(60) Continuation of application No. 08/601,865, filed on Feb. 15, 1996, now Pat. No. 5,744,122, which is a division of application No. 08/286,745, filed on Aug. 5, 1994, now Pat. No. 5,580,715.

(51) Int. Cl.[7] ............... A61K 49/00; A61K 48/00; C12N 5/00; C12N 15/00

(52) U.S. Cl. ............... 424/9.2; 424/93.2; 435/325; 435/372; 435/455

(58) Field of Search ............... 800/8, 10, 11; 435/325, 372, 5, 6, 91.2, 91.33, 69.1, 366, 455; 424/9.2, 93.2

(56) References Cited

U.S. PATENT DOCUMENTS 5,744,122 A * 4/1998 McGrath et al. ............ 424/9.2

* cited by examiner

*Primary Examiner*—Deborah Crouch
(74) *Attorney, Agent, or Firm*—Paula A. Borden; Bret E. Field; Bozicevic, Field & Francis, LLP

(57) ABSTRACT

The presence of clonal macrophages in pre-cancerous and cancerous tissue represents an early stage of the disease in which clonal expansion of macrophages occurs due to HIV integration or other genetic mutation. Clonally expanded macrophages induce proliferation of surrounding tissue leading to cancerous tumor growth. The invention provides methods and kits for diagnosis of HIV- and non-HIV-associated clonal expansion of macrophages in pre-cancerous and cancerous tissue. The invention also provides methods for the treatment of cancers induced by clonal macrophage expansion and proliferation of surrounding tissue.

12 Claims, 1 Drawing Sheet

DIAGNOSIS AND TREATMENT OF CANCER HAVING CLONAL MACROPHAGE INVOLVEMENT

This application is a continuation of U.S. patent application Ser. No. 08/601,865, filed Feb. 15, 1996 now U.S. Pat. No. 5,744,122. Which is a divisional of U.S. Ser. No. 08/286,745 filed Aug. 5, 1994 now U.S. 5,580,715.

STATEMENT AS TO FEDERALLY SPONSORED RESEARCH

This invention was made at least in part with funds from the Federal government, and the government therefore may have certain rights in the invention.

FIELD OF THE INVENTION

The field of the invention relates to cancer therapy; human immunodeficiency virus; a recombinant macrophage; methods of diagnosis of macrophage involvement in cancer development; kits for use in diagnosis; and methods of treatment for cancer involving macrophage-induced tissue growth.

BACKGROUND OF THE INVENTION

Of the approximately 36,000 new cases of lymphoma diagnosed in the United States in 1992, between 8 and 27-o are estimated to have occurred in HIV-infected individuals (Gail, M. H. et al., *J Natl Can Int* (1991) 83:695–701). Thus, HIV-related lymphoma represents a major clinical problem for physicians involved in the care of HIV-infected individuals.

The biology of AIDS lymphoma is controversial and appears complex. Early in the AIDS epidemic high grade non-Hodgkin's lymphoma (NHL) began to appear in individuals at risk for the development of AIDS (Ziegler, J. et al., *N Eng J Med* (1984) 311:565–570). However, in the past several years, the incidence of NHL in HIV-infected individuals has increased (Harnly, M. E. et al.,*Am J. Epi* (1988) 128(2):261–267; Levine, A. et al., *Ann Intern Med* (1984) 100:7–13). It is clear that as the AIDS epidemic expands, non-Hodgkin's lymphoma will become a continually more important health problem in HIV-infected individuals. As treatment for the underlying HIV disease becomes more successful and as patients survive for longer periods of time in-the absence of opportunistic infections, more cases of lymphoma will probably appear in this patient population.

The non-Hodgkin's lymphomas that develop in HIV-1 infected individuals fall into two main subcategories: the large cell lymphomas and the small non-cleaved cell Burkitt's lymphomas (Ziegler, J. et al., 1984, supra; Knowles, D.M. et al., Blood (1989) 73:792–799; Bermudez, M. et al.; *Am J Med* (1989) 86:71–76; Gill, P. et al., *J Clin Oncol* (1987) 5:1322–1328; Kaplan, L. D. et al, *JAMA* (1989) 261:719–724; Knowles, D. M. et al., *Ann Intern Med* (1988) 108:744–753; Lowenthal, D. A. et al., *Cancer* (1988) 61:2325–2337). Both major classes of lymphoma are high grade 5neoplasms and are predominantly of B-cell origin (Ziegler, J. et al., 1984, supra.; Subar, M. et al., Blood (1988) 72:667–671.); however, T-cell lymphomas may also be increasing in frequency (Presant, C. A. et al., *Cancer* (1987) 60:1459–1461; Nasr, S. et al., *Cancer* (1988) 61:947–951; Herndier, B. et al., VII Intl Conference of Acquired Immunodeficiency Syndrome (AIDS), Florence, Italy, Jun.16–21, 1991). In HIV disease lymphomas tend to be diffusely aggressive, with approximately 90% originating from B-cells and 5–10% derived from T-cells. Approximately one-half of the large cell lymphomas are herein termed "mixed immunophenotype" lymphomas as they contain a mixture of B-cells, T-cells, and macrophages. AIDS-associated non-Hodgkin's lymphomas are commonly characterized by their very high rates of extranodal (85–97%) (Kaplan, L. D. et al., *JAMA* (1989) 261:719–724; Burkes, R. L. et al., *Arch Intern Med* (1986) 146:913–915; Balasubramanyam, A. et al., *Chest* (1986) 90:243–246; Guarner, J. et al., *Arch Pathol Lab Med* (1987) 111:254–256; Kaplan, L. et al., *Ann Intern Med* (1989) 110:162; Friedman, S. L., *Gastroenterol Clin North Am* (1988) 17:465–486) and central nervous system involvement (35k) (Baumgartner, J. et al., *J Neurosurc* (1990) 73:206–211; Formenti, S.C. et al., *Cancer* (1989) 63:1101–1107; Ciricillo, S. et al., *J Neurosurq* (1990) 73:720–724), as well as their poor response to current chemotherapy protocols (Kaplan, L. D. et al., (1989) supra; Bermudez, M. et al.,*Am J Med* (1989) 86:71–76; Gill, P. et al., *J Clin Oncol* (1987) 5:1322–1328; Urba, W. et al., *Journal of the National Cancer Institute* (1990) 10:29–37; Kaplan, L. D. et al., JCO (1991) 9(6):929–940).

Lymphomas, in general, are a heterogeneous group of malignancies. Their biologic behavior ranges from indolent, requiring no therapy, to aggressive malignancies with few long-term survivors. The behavior of lymphoma is influenced by the immune status of the host. The risk of B-cell lymphoma is dramatically increased in individuals with defects of cell-mediated immunity. The best characterized of these groups is immunosuppressed allograft recipients, whose risk of developing lymphoma is between 50 and 60 times that of the general population. These individuals develop a spectrum of lymphoproliferative diseases ranging from typical monoclonal immunoblastic lymphoma to an aggressive form of polyclonal lymphoproliferative disease (Frizzera, G. et al., *Cancer Res* (1981) 41:4262–4279; Hanto, D. W. et al., *Cancer Res* (1981) 41:4253–4261; Hanto, D. W. et al., *Ann Surg* (1983) 198:356–369) often associated with Epstein Barr Virus (Hanto, D. W. et al., (1981) supra; Penn, I., *Transplant Proc* (1983) 15 (suppl 1):S2790–S2797; Shearer, W. T. et al., *N Engl J Med* (1985) 312:1151–1159) infection. Clinically, lymphoma in these individuals presents aggressively at extranodal sites indicating a common feature between HIV-associated lymphomas and the molecular and clinical characteristics of the allograft-associated lymphomas.

The primary means of HIV lymphoma diagnosis remains microscopic examination of hematoxylin and eosin-stained sections from formalin-fixed tissue. Over time, pathologists have used clinical presentations, autopsy follow-up, and trial and error to develop histologic methods a of diagnosing and categorizing cancer. Missing a histologic diagnosis of cancer or 'over-calling' a cancer and subjecting a patient to cancer therapy are sufficient incentives for providing accurate diagnosis. Traditional histologic methods can be enhanced by phenotypic and, particularly, genotypic analyses of lymphomas where the discerned molecular changes of the affected tissue point to an alternative form of treatment.

SUMMARY OF THE INVENTION

The invention. relates to a method of diagnosing clonal macrophage involvement in HIV-associated and non-HIV-associated lymphomas or other cancers using genotypic analysis as well as a kit for such diagnostic method. The invention also relates to a method of treating macrophage-induced cancer. The invention also relates to a recombinant macrophage useful in vitro and in vivo methods of screening for therapeutic agents useful in treating macrophage-induced cancer.

The discovery that HIV lymphomas are frequently associated with clonal macrophage involvement and that the macrophage has HIV DNA integrated upstream of a known oncogene, c-fes (c-fes/fps), is disclosed. As described in detail below, macrophage clonality is associated with many HIV-related lymphomas. Macrophage clonality can be associated with non-HIV-related lymphomas as well. Expansion of macrophages may enhance growth of surrounding tissue by secretion of cytokines; the cytokine Interleukin-6 has been shown to cause growth of myeloma and hybridoma cells (Woodruff, C. et al., *DNA and Cell Bioloqy* 11:587–592). Diagnosis of macrophage clonality and treatment targeting macrophages offers a new direction in cancer therapy. Disclosed are diagnostic methods and kits as well as therapeutic methods useful in the battle to overcome clonal macrophage-induced HIV lymphomas and clonal macrophage-induced cancers in general.

Accordingly, in one aspect, the invention features a method of diagnosing the presence of clonally expanded macrophages in a suspected cancerous tissue of a mammal by first obtaining a sample of the tissue suspected of being cancerous followed by isolation of DNA from the tissue by standard techniques known to those skilled in the art of molecular biology. The presence of clonal DNA in the isolated DNA is determined by standard techniques including but not limited to HIV integration site analysis by IPCR (Shiramizu, B. et al., *Cancer Res* (1994) 54:2069–2072); RFLP (Restriction Fragment Length Polymorphism) analysis of genomic sequences near common sites of viral (e.g., HIV) integration; or immunoglobulin (Ig) gene rearrangement analysis (Levy, R. et al., *J Exy Med* (1977) 145:1014–1028). Preferentially, this analysis includes mixing known quantities of control monoclonal DNA and control polyclonal DNA such that, following Southern analysis, the DNA band intensity of a 5% monoclonal mixture is determined and used as a standard against which the clonality of the test DNA is compared. Using this technique, monoclonal tumors are those defined as having more than a 5% monoclonal DNA component. Preferably, the technique of inverse polymerase chain reaction (IPCR) used to determine the clonality of a tissue sample containing integrated HIV is a valuable diagnostic tool and is defined in detail below.

The invention also features a kit for the diagnosis of macrophage-induced pre-cancerous and cancerous tissue as tissue containing greater than 5% monoclonal DNA from macrophages. The kit of the invention features nucleic acid primers for amplifying DNA of an HIV-containing cell (e.g., a macrophage). The nucleic acid primers for amplification of HIV-containing DNA preferentially hybridize to regions of the 5' and /or 3' long terminal repeats (LTRs) such that DNA synthesis is primed in opposite directions for IPCR analysis. The kit also includes a labeled (e.g., radiolabeled; biotinylated; or other standard label) probe for the RFLP analysis of genomic DNA for clonality where priming of HIV sequences is not desirable (e.g., in non-HIV-related cancers). Such a probe hybridizes to a genetic locus which is a common site of viral integration leading to cellular proliferation.

The diagnostic method of the invention features comparing the clonality of test DNA to control HIV-containing DNA to indicate involvement of HIV-containing clonal cells (e.g., clonal macrophage) in the tissue morphology. The involvement of macrophages is determined by initial sorting into cellular subpopulations. (by fluorescence activated cell sorting (FACS) technique or macrophage adherence to glass or plastic; or other technique well known in the art) followed by DNA analysis. Alternatively, analysis of DNA from a mixed cellular population is performed followed by dual staining or in situ hybridization of a tissue preparation to correlate clonal HIV with the macrophages.

The diagnostic method of the invention also features analysis of the clonality of non-HIV-associated macrophages. The method involves isolating test DNA from a mixture of cells or a pre-sorted subpopulation of macrophages from pre-cancerous or cancerous tissue followed by RFLP analysis of the test DNA. RFLP analysis of the invention utilizes a nucleic acid probe that hybridizes to a genomic sequence encoding a common viral (e.g., HIV) integration site associated with cellular proliferation upon viral integration. For example, HIV integration into genomic DNA in the z exon of the fur gene has been observed in both T-cells (Shiramizu, B., et al. (1994), supra) and in macrophages as described herein.

Using the diagnostic method of the invention, the absence of HIV clonality can indicate a non-HIV-associated clonal macrophage involvement in the tissue morphology. The absence of both HIV and macrophage involvement is also discernable using the kit of the invention. The diagnosis of macrophage involvement provides the clinician with powerful information for designing an appropriate treatment regimen for the patient.

The invention features a macrophage having integrated in its genome a transcriptional/translational controlling sequence operably attached to a cell proliferation gene such that expression of the cell proliferation gene results in (expansion) of the macrophage. Cell proliferation can be the result of substantially increased expression of a cytokine gene or other cell proliferation gene such as an oncogene. For example, integration into the z exon of the macrophage fur gene of a strong promoter and/or enhancer element (e.g., an HIV genome; a defective HIV genome wherein the enhancer region of an HIV 3' LTR is functional; the enhancer region of an HIV 3' LTR; or other promoter or enhancer element capable of substantially increasing expression of a nearby gene (whereby nearby is meant within about 12 kb, preferably about 10 kb, or more preferably about 5 kb of the transcriptional start site) such that expression of the downstream c-fes/fps gene is substantially increased relative to c-fes/fps expression in a macrophage having no promoter or enhancer element integrated within it. Integration of a DNA sequence encoding a strong promoter and (optionally an enhancer element) operably attached to a growth promoting cell proliferation gene into the macrophage genome is accomplished by standard molecular biology techniques (e.g., delivery of the transfecting DNA in liposomes) (see e.g., Sambrook et al., *Molecular Cloning: A Laboratory Manual*, Green Publishing Associates, Cold Spring Harbor Laboratory Press, 1989; and Ausubel et al., Current *Protocols in Molecular Biology*, John Wiley & Sons, new York, 1989). Recombinant macrophages are screened for increased c-fes/fps expression by techniques described herein. Alternatively, the transcriptional/translational controlling regions are fused to a cell proliferation gene on a DNA expression cassette which is integrated into the macrophage genome. Expression of the cell proliferation gene of the cassette also results in cell proliferation. Recombinant macrophages are also screened for the ability to enhance cell proliferation relative to non-recombinant macrophages when introduced into a population of B- and/or T-cells.

Macrophages which express increased levels of cell proliferation controlling gene such as the oncogene c-fes/fps are useful for screening therapeutic agents in vitro for the ability to inhibit growth of such macrophages. The screening method of the invention provides cultured recombinant macrophages expressing a substantially increased level of c-fes/fps in an appropriate culture medium. To the cultured recombinant macrophages is added a therapeutic agent in an appropriate formulation for delivery of the therapeutic agent to the recombinant macrophage. The effect of administration of the agent is monitored as reduced cell growth, reduced cell viability, reduced c-fes/fps expression, and/or reduced cytokine expression. Methods of monitoring cell growth and viability are well known in the art. Methods of monitoring c-fes/fps and cytokine expression are described herein. Therapeutic agents which cause reduction in the monitored phenotypes are selected as candidate compounds or formulations for treatment of macrophage-induced cancers such as those listed in Table II.

The invention features a method of screening candidate therapeutic agents in vivo for the ability to substantially eliminate a recombinant macrophage (e.g., a clonally expanded macrophage having a transcription controlling sequence integrated for the increased expression of a cell proliferation gene) from the host. The recombinant macrophage is injected into the appropriate tissue of the host (e.g., the spleen, the peripheral blood, the skin, or the bone marrow) and growth of a tumor containing the recombinant macrophage is monitored. To the host is then administered a candidate therapeutic agent in a formulation for preferential uptake by a macrophage, wherein the administering is performed at a dose, an interval, and for a duration that is sufficient to substantially eliminate the recombinant macrophage from the host.

Another feature of the invention is screening or a candidate therapeutic agent for treatment of cancers induced by the presence of clonally expanded macrophages. The screening method involves transplantation of mammalian tumor tissue containing clonally expanded macrophages (such as a recombinant macrophage which contains a growth promoting cell proliferation gene operably attached to a functional transcriptional controlling region such as a promoter/enhancer region) into a mammal (such as a severe combined immumodeficiency (SCID) mouse). A cancer is allowed to develop in the mammal containing the implanted tissue. A pharmaceutically effective amount of a candidate therapeutic agent is administered to the mammal to determine if administration of the agent results in reduction in the size of the tumor, reduction in clonal macrophage viability, or reduction in clonal macrophage proliferation.

Another feature of the invention is a method of treatment of clonal macrophage-involved cancer by first determining the presence of a clonally expanded macrophage in the cancer. Second, the macrophage is substantially eliminated from the cancerous tissue by administering to the mammal (preferably a human) harboring the cancerous tissue, a therapeutic agent that is in a formulation for preferential uptake by a macrophage. The administering is performed at a dose, at an interval and for a duration that is sufficient to substantially eliminate the macrophages (including the clonally expanded macrophages) from the mammal followed by discontinuation of the administering of the therapeutic agent such that the macrophage population of the mammal is regenerated.

Another feature of the invention is the treatment method described above wherein the therapeutic agent is DNA encoding antisense MRNA of a cell proliferation gene. The target cell proliferation gene is one positioned near (i.e., within 12 kb, preferably within 5 kb in distance from) a common site of HIV integration wherein the common site of HIV integration is shown by the diagnostic method of the invention to be clonally mutated. Introduction of the antisense-encoding DNA into the macrophage genome and expression of the antisense MRNA reduces expression of the cell proliferation gene.

Another feature of the invention is a therapeutic agent comprising DNA encoding a mutant form of a cell proliferation gene such that recombination into the endogenous cell proliferation gene of the macrophage genome results in the mutation being incorporated into the genome. The mutation of the cell proliferation gene is designed such that gene expression is substantially eliminated or that the expressed gene produces a substantially nonfunctional gene product.

Those skilled in the field of molecular biology will understand that any of a variety of conventional gene transfer methods may be used for introducing genes into cells. For example, physical methods for the introduction of DNA into cells include microinjection (see, e.g., Capecchi et al., *Cell* 22:479, 1980), electroporation (see, e.g., Reiss et al., *Biochem. Biophys. Res. Commun.* 137:244, 1986) and other standard methods. Chemical methods such as coprecipitation with calcium phosphate and incorporation of DNA into liposomes also have been used to introduce DNA into mammalian cells, particularly macrophages as described herein. Finally, delivery of nucleic acids into mammalian cells can be executed through the use of viral vectors, in particular those derived from murine and avian retroviruses (see, e.g., Gluzman et al., *Viral Vectors*, Cold Spring Harbor Laboratory, Cold Spring Harbor, N.Y., 1988).

The invention can utilize a commercially available cytotoxic therapeutic agent such as trichosanthin (Lifson, J. D. et al., USPN 4,795,739; USPN 4,869,903; McGrath, M. S. et al., *PNAS* (1989) 86:2844–2848), alpha- or beta-momorcharin (Lifson, J. D., et al., supra), other single-chain ribosome inactivating protein or other cytotoxic agent well known in the art of HIV inhibition or cancer therapy. The cytotoxin may comprise multiple agents such that the combined actions of the agents results in cytotoxicity.

Trichosanthin is a plant protein obtained from the *Trichosanthes kirilowii* root tuber. It has homology to the amino acid sequence of Ricin A chain and may have ribosome-inhibitory properties similar to ricin and various single-chain ribosome-inhibitor proteins, such as momorcharin, pokeweed anti-viral protein (PAP), wheat germ inhibitor, and gelonin (Xuejun) (Lifson, J. D., et al., supra). Trichosanthin and momorcharin inhibit expression of HIV antigens in human blood cells including macrophages (Lifson, J. D., et al., supra).

Examples of other cytotoxic or proliferation-modulating agents include daunomycin, mitomycin C, daunorubicin, doxorubicin, 5-FU, cytosine arabinoside, colchicine, cytochalasin B, bleomycin, vincristine, vinblastine, methotrexate or the like. Also of interest are toxic agents which may be derived from microorganism or plant sources. Examples include the toxic subunits of naturally occurring toxins such as ricin, abrin, diphtheria toxin, saporin, and the like. Illustrative toxic subunits include the A chains of diphtheria toxin, enzymatically active proteolytic fragments from *Pseudomonas aeruginosa* exotoxin-A, ricin A-chain, abrin A-chain, modeccin A-chain, and proteins having similar activity found in various plants such as the plants *Gelonium multiflorum, Phytolacca Americana*, Croton, Tiglium, Jatropha, Curcas, Momordic, Charantia, Reachan, the toxin saporin from *Saponaria officinalis* (Thorpe et al. *J. National Cancer Institute* (1985) 75:151), the Chinese cucumber toxin, trichosanthin (Yeung et al. *Intl. J. of Peptide Protein Res.* (1985) 27:325–333). Mutant species of the toxins also may be used, for example, CRM 45 (Boquet et al. *Proc. Natl. Acad. Sci. USA* (1976) 73:4449–4453).

The cancer treatment method of the invention features a liposome preparation containing within the liposome a macrophage-specific cytotoxin or a broad-spectrum cytotoxic agent. Such cytotoxin-containing liposome is prepared to be a size appropriate for the uptake of the cytotoxin-containing liposome preferentially by a macrophage. Targeting of the cytotoxin-containing liposome to a macrophage provides specificity of delivery and increased uptake. Targeting is accomplished by incorporation or attachment of a macrophage-specific antibody such as anti-CD14 to the liposome. Appropriate lipids and other agents and methods for the preparation of therapeutic liposomes are well known in the art (see e.g., Martin, F. J. and Papahadjopoulos, D., *J. Biol. Chem.* 257:286–288, (1982); Szoka, F. and Papahadjopoulos, D., Ann. *Rev. Biophys. Bioeng.* 9, 467–508, (1980); and Ostro, M. J. (ed) *Liposomes From Biophysics to Theraueutics*, Marcel Dekker, Inc., New York, 1987).

The cancer treatment method of the invention additionally features an anti-macrophage cell surface antibody covalently attached to a cytotoxic agent such that the cytotoxic agent is preferentially taken up by a macrophage following attachment of the cell surface antibody-cytotoxin complex to a macrophage cell surface marker. Uptake of the complex is by a phagocytic process normal to the macrophage.

The proliferation-modulating agent and the targeting agent which provides binding to the extracellular matrix can be linked, usually by a bond which is cleavable, either intra- or extracellularly by reduction hydrolysis enzymatically, or by a bond which is acid labile. The type of linkage used depends upon a number of factors, but particularly the nature of the proliferation-modulating agent. For example, where the agent is one which must be internalized by a cell to have an effect, such as a toxin molecule or toxin A chain, it is preferable that the linkage to the targeting moiety can be cleaved. The targeting moiety can be linked to a drug either directly or indirectly by carrier molecules such as serum albumin (particularly human serum albumin), polyaminoacids, dextran, and the like, by methods well known to those skilled in the art. The use of a carrier molecule permits binding of multiple molecules of the proliferation-modulating agent to the linker molecule, preferably 10 to 30 molecules per molecule of carrier molecule for an antiproliferative compound, or 1 to 2 molecules per molecule of carrier molecule for a toxin molecule.

The type of linkage used can also be dictated by the cell type which is the ultimate goal of the proliferation modulating activity thus preferably the linkage is a Ph labile or acid labile link between the targeting moiety and the proliferation-modulating moiety in cases where the-cells have phagocytotic properties, for example, fibroblasts and macrophages. Also of interest are peptide linkages which would be susceptible to hydrolysis by enzymes which may also be present in the extracellular matrix. Convenient linkages thus include disulfides, imides, hydrazones, amides and the like.

The cancer treatment method of the invention additionally features the complementary treatment of the non-macrophage cells of the tumor by conventional cancer therapy methods such that both the clonally expanded macrophage of the tumor and the non-macrophage cells of the tumor are each substantially ablated.

By "clonal macrophage" or "clonally expanded macrophagen" is meant identical copies of a macrophage arising from a single progenitor macrophage.

By "clonality of DNA" is meant the degree to which DNA isolated from a cell population is the same as determined by the pattern of discernable DNA characteristics such as RFLP (restriction fragment length polymorphism), gene rearrangement by Southern analysis, IPCR, or other techniques known to those skilled in the art. Accordingly, a tissue sample is designated as having a monoclonal macrophage component if practice of the diagnostic method of the invention results in a distinct HIV-specific and/or macrophage-specific DNA band pattern of equal or greater intensity than a 5% control sample.

By "5% control sample" is meant a sample of known polyclonal DNA to which has been added a sample of known monoclonal DNA to constitute 5% of the total DNA.

By "promoter" is meant minimal sequence sufficient to direct transcription. Also included in the invention are those promoter elements which are sufficient to render promoter-dependent gene expression controllable for cell-type specific or inducible by external signals or agents; such elements may be located in the 5' or 3' regions of the native gene.

By "integrated into the genome" is meant exogenous DNA (such as an expression cassette or viral sequence) that is linearly incorporated within the genomic DNA chain of a cell (such as a macrophage) and is connected at each of its termini to the genomic DNA. Exogenous DNA encoding an expression cassette is integrated such that functional RNA or proteins are produced by the encoded sequences. An exogenous viral sequence is integrated such that expression of nearby endogenous By "enhancer" is meant minimal sequence sufficient to enhance transcription substantially above wild type levels. Also included in the invention are those enhancer elements which are sufficient to enhance promoter-dependent gene expression controllable for cell-type specific or inducible by external signals or agents; such elements may be located in the 5' or 3' regions of the native gene.

By "pharmaceutically active amount" is meant an amount of an agent (such as a therapeutic agent) that when administered to a cell or a mammal results in a desired physiological effect (such as cytotoxicity, reduced viability, or substantially reduced proliferation).

By "substantial increase" or "substantially above" is meant an increase in expression, transcription or other process above the wild type level of that process where the increase is at least approximately 50% above wild type.

By "substantial decrease" or "substantial reduction" is meant a decrease or reduction in expression, transcription, or a measurable phenotypic characteristic that is approximately 80% of the wild type level, preferably reduced to approximately 50% of the wild type level, or more preferably reduced to approximately 10% or less of the wild type level.

By "substantially eliminated" or "substantial ablation" is meant a decrease in cell number such that less than approximately 50% of the cells remain viable, preferably less than approximately 20% of the cells remain viable, or more preferentially less than 10% of the cells remain viable.

By "substantially reduced viability" is meant a decrease in the number of living cells in a population of cells relative to a control population such that less than approximately 50% of the cells remain viable, preferably less than approximately 20% of the cells remain viable, or more preferentially less than 10% of the cells remain viable.

By "pre-cancerous tissue" is meant mammalian tissue which is hyperplastic by histological examination and surgical-pathological evaluation well known to those skilled in the art of pathology.

By "cancerous tissue" is meant mammalian tissue which is no longer under the normal control of growth regulators. The cancerous nature of mammalian tissue is determined by surgical-pathological evaluation well known to those skilled in the art of pathology.

By "antisense" is meant nucleic acid wherein the non-coding strand of a target gene of interest is positioned for expression in a construct such that when expressed as MRNA, the single stranded antisense MRNA is complementary to and can hybridize to the MRNA of the target gene modulating its utilization. The sequence complementary to a sequence of the messenger RNA will usually be at least about 15 nucleotides, more usually at least about 20 nucleotides, preferably about 30 nucleotides or more, and more usually being fewer than 1000 nucleotides in length.

The particular site(s) to which the antisense sequence binds and the length of the antisense sequence will vary depending upon the degree of inhibition desired, the uniqueness of the sequence, the stability of the antisense sequence, or the like. Therefore, these factors will be determined empirically based on the experience obtained with a particular antisense sequence.

By "operably attached" is meant a nucleic acid sequence to be expressed being fused at the 5' end to a functional promoter element including transcriptional and translational (where applicable) initiation sites and being fused at the 3, end to a functional transcriptional and translational (where applicable) termination sequence.

By "nucleic acid primer" is meant a single stranded nucleic acid sequence, preferably DNA, that hybridizes to a nucleic acid sequence of interest for priming of DNA synthesis by DNA polymerase. The nucleic acid primers of the invention are designed for use in the polymerase chain reaction method and inverse polymerase chain reaction method (Shiramizu, B. et al. (1994), supra) and as described herein.

By "labeled nucleic acid probe" is meant a single strand nucleic acid sequence to which is attached a label (such as a radiolabel; a biotinylation moiety; or other label known in the art and useful in Southern and Northern analyses). The nucleic acid sequence of the labeled probe used in the diagnostic method of the invention hybridizes to a genomic sequence near (i.e., within 5 kb, preferentially within 1 kb) a common HIV integration site. HIV integration at the site is associated with increased proliferation of the infected cell. An example of such a common integration site is the z exon of the fur gene where HIV integration is associated with macrophage proliferation (as described herein) or T-cell proliferation (Shiramizu, B. et al. (1994), supra)

By "cell proliferation" is meant increased cell growth in a test population above the rate of cell growth (e.g., cell division) of a control population such that cell growth is 20% above, preferably 50% above, or more preferably greater than 100% above a control population.

By "gene associated with cell proliferation" is meant a cell growth promoting gene (such as an oncogene) which when activated due to viral integration or other mutation results in increased cell proliferation. Cell proliferation genes include without limitation oncogenes such as c-fes/fps, ras, c-myc and others well known in the art; and genes encoding cytokines such as IL-6 and IL-10. An activated oncogene means an oncogene which increases the probability of the development of neoplasms (particularly malignant tumors) in a mammal (particularly a human). A gene associated with cell proliferation also includes a cell growth suppressing gene such that decreased gene expression of a suppressor gene results in cell proliferation.

By "essentially non-functional mutated form of gene" is meant a gene or its gene product that is expressed or functions at 50%, preferably 20%, or more preferably less than 10% of wild type level.

By "preferential uptake by a macrophage" is meant a macrophage able to incorporate an agent to a greater extent (20% greater, preferably 50% greater, or more preferably more than 100% greater extent) than cells of other cell types in the cell culture or in the mammal.

By "kit" is meant a combination of physical elements such as specific primers, labeled probes and other elements useful to practice the invention. The diagnostic kit of the invention comprises elements useful for the diagnosis of clonal macrophages in a mammalian tissue sample.

By "macrophage" is meant a cell of the monocyte/macrophage lineage which is found in the spleen or has differentiated into a tissue macrophage. These cells include follicular dendritic cells (FDC), dendritic cells, Langerhans cells, as well as other tissue macrophages. The macrophage described herein is a non-tingible body macrophage not associated with scavenging cellular debris in the tissue.

By "HIV" is meant a human immunodeficiency virus of strains HIV-1, HIV-2, or other variants.

The methods of the invention and the kit of the invention are preferably designed for the diagnosis and treatment of clonal HIV- and non-HIV-associated macrophage-induced cancer in a human.

Other features and advantages of the invention will be apparent from the following description of the preferred embodiments thereof, and from the claims.

BRIEF DESCRIPTION OF THE DRAWING

The drawing will first be described.

Drawing

DESCRIPTION OF THE PREFERRED EMBODIMENTS

Figure 1:
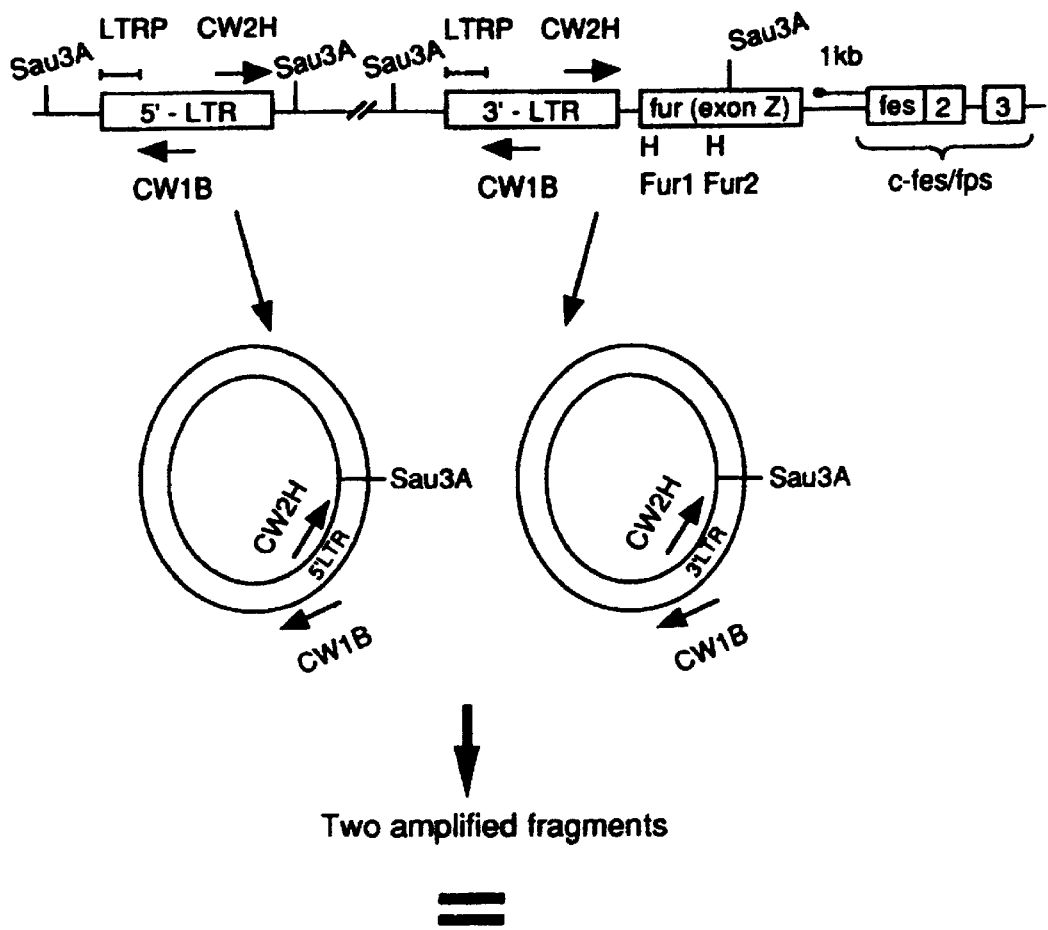
FIG. 1 is a schematic diagram of the IPCR method to detect integration sites. Primers CW1B and CW2H flank the LTR region in the opposite direction. The sequence of the primers and probes in the box. The location of the primers and probes is indicated as arrows above and below the. genetic map of the fur gene integration site.

There now follows-a description of the compositions and methods for determining the presence of clonal HIV in a tissue sample as well as descriptions of techniques useful in carrying out the invention. The examples below are provided for the purpose of illustrating the invention, and should not be construed as limiting.

Experimental Data: Results

HIV and the Pathogenesis of Non-B-Cell Malignancies

As described above, some AIDS-associated non-B-cell lymphomas contain clonal forms of HIV. It is useful to determine the cell type that is clonally expanded in order to evaluate the necessary therapy. To determine the presence and clonal nature of HIV in pre-cancerous and cancerous tissue, two mixed immunophenotype lymphomas and one angioimmunoblastic lymphadenopathy with dysproteinemia (AILD) specimens were analyzed. Southern blot analysis identifying a high level of HIV in three of these cases was performed as described in Materials and Methods. These lymphomas were found to have a single predominant form of HIV present within the tumor. All three of the tissue specimens had mixed immunophenotype morphology; two of them had no clonal B or T lymphocytes, whereas one had a clonal population of T-cells.

In order to map the integration site of the HIV sequences within these lymphomas, a process called inverse PCR (IPCR) was performed (Shiramizu, B. et al., (1994) supra). A schematic diagram of the IPCR technique is provided in FIG. 1. In this technique the integration sites of clonal forms of HIV were amplified by utilizing PCR primers complementary to sequences within the HIV LTR facing outward from each other, followed by restriction digestion, ligation, and DNA synthesis.

As shown in FIG. 1, when a clonal form of HIV is present within a tumor, a simple band pattern of one or two PCR bands will generally appear, each band representing an LTR with flanking cellular genomic sequence. The integration site from these mixed immunophenotypic specimens was mapped to a segment of the fur gene present on chromosome 15 just 5' to the c-fes/fps oncogene. This is the same integration site observed in a clonal HIV-associated T-cell lymphoma (Shiramizu, B. et al., (1994) supra) suggesting that integration of HIV upstream of the c-fes/fps oncogene leads to cellular expansion. IPCR was performed on tumor and non-tumor involved tissue from these three tumors as compared to the previously described T-cell lymphoma. Clonal IPCR products were amplified from these tumors whereas uninvolved lymph node and spleen from two of the cases showed no amplifiable sequences. Southern analysis using an internal LTR gene probe hybridized to both amplified IPCR products from each tumor, showing that each product had an LTR sequence. Two fur probes representing oligonucleotides at both the 5' and 3' ends of the 3' exon of fur were used in a Southern analysis of these IPCR products. One LTR-containing IPCR product from each case hybridized with this fur probe indicating that HIV had integrated in the 3' exon of the fur gene. Sequence analysis of one of these tumors confirmed the localization to this segment of the fur gene. The integration site for one specimen mapped to base pair position 301 and for another specimen mapped to base pair 1652 of the 2200 base pair 3' exon of fur.

To determine the sensitivity of the IPCR analysis, DNA from the original T-cell lymphoma (Shiramizu, B., et al., (1994), supra) was serially diluted into DNA extracted from a hyperplastic lymph node from the same patient. The IPCR technique has a sensitivity of between 2 and 5 percent in that clonal forms of integrated HIV would only be amplifiable if they represented between 2 and S percent of the specimen (Shiramizu, B. et al. (1994), supra). No forms of IPCR product have been observed in hyperplastic nodes or splenic tissue from HIV-infected individuals.

Clonal Forms of HIV are Found in Non-B-Cell Lymphomas

In order to test whether clonal HIV involvement would be common in non-B-cell lymphomas, an IPCR analysis was done on a spectrum of non-B-cell malignancies. The IPCR method is detailed in Materials and Methods. This spectrum included specimens from patients with mycosis fungoides, cutaneous T-cell lymphoma, AILD, Hodgkin's disease, and mixed immunophenotype lymphomas. Table I lists the results of the IPCR analysis.

TABLE I

Summary of Cases and IPCR Results

| Case | Sample | Dx | IPCR | FUR |
|---|---|---|---|---|
| 1. | DT | MF (cutaneous) | 2 Bands | — |
| 2. | GC-2 | MF (cutaneous) | — | |
| 3. | EP | Lym (cutaneous) | — | |
| 4. | HK | Lym (cutaneous) | 1 Band | — |
| 5. | JW | Lym (cutaneous) | 1 Band | — |
| 6. | RB | Lym (cutaneous) | 2 Bands | N.D.[1] |
| 7. | TPF | Lym (cutaneous) | 1 Band | — |
| 8. | WC | Lym (cutaneous) | 1 Band | — |
| 9. | BR | T-cell (node) | 2 Bands | + |
| 10. | FR | Mixed immunophenotype | 2 Bands | + |
| 11. | AP | Mixed Immunophenotype | 2 Bands | + |
| 12. | BW | Mixed immunophenotype | 2 Bands | + |
| 13. | GH | AILD | 2 Bands | + |
| 14. | CL | AILD | — | |
| 15. | TB | AILD | 1 Band | + |
| | | KS (brain) (adrenal) | — | |
| 16. | GS | Hodgkin's | — | |
| 17. | JF | Hodgkin's (kidney) | 1 Band | — |
| 18. | UM | Hodgkin's | 2 Bands | — |

[1]N.D.: not done.

The results are tabulated with the number of IPCR bands, from each sample, where MF: mycosis fungoides; Lym: lymphoma; AILD: angioimmunoblastic lymphadenopathy; KS: Kaposi's sarcoma. Additional tissue was available from three cases (9: uninvolved node; 15: uninvolved adrenal and KS of brain; 17: uninvolved kidney) which were used as internal negative controls. The results of hybridization to the fur probe (column 5) are listed as positive or negative for samples which had IPCR bands.

The data in Table I indicate that fourteen of eighteen cases analyzed had clonal forms of HIV present within the tumor DNA. In each case where clonal forms of HIV were detected, one or two IPCR products were amplified. The size of amplified bands varied between specimens making it unlikely that the bands were a PCR artifact. In some cases immunophenotypic data confirmed the presence of HIV in cells present within the tumor. The Hodgkin's disease specimen UM was a syncytial variant Hodgkin's disease where all of the tumor cells were Reed-Sternberg cells which are related to cells of the macrophage lineage. These cells stained with anti-HIV-p24 antibody and a clonal form of HIV was identified by IPCR. All of the IPCR products also hybridized with an HIV LTR probe in Southern analysis. Six of 13 IPCR products hybridized with the previously described fur probes indicating that these six non-B-cell lymphomas had a clonal form of HIV integrated just 5' to the c-fes/fps oncogene.

Clonal HIV involvement was examined in four cases of Kaposi's Sarcoma. One in four of the specimens exhibited clonal HIV IPCR products and HIV p24 analysis localized HIV expression to macrophages adjacent to tumor cells.

c-Fes/fps is ExDressed in Tumor Tissue

Northern blot analysis was performed on RNA extracted from-cases 9 and 10 of Table I above to determine whether c-fes/fps was expressed in tumor tissue having HIV integrated upstream of the c-fes/fps gene. The Northern blot showed the presence of a 3 kilobase pair (kb) c-fes/fps message from tumor MRNA, whereas the same message was not obtained form non-tumor MRNA. The 3 kb message is a size appropriate for the c-fes/fps MRNA which encodes a 92 kilodalton (Kd) tyrosine kinase (not shown). To determine whether the c-fes/fps MRNA would give rise to Fes protein, a monoclonal anti-Fes antibody was obtained from ATCC (HB8595) and used in a series of immunohistochemical studies. Fes protein was detected frequently in tumor cells present in one of the mixed immunophenotype macrophage-rich lymphomas, whereas it was detected infrequently within a follicular hyperplastic HIV-infected lymph node.

A clonal form of HIV was also present within AILD, a disease process thought to represent a pre-lymphomatous state. Histologically the AILD GH specimen showed localization of the anti-p24 antibody to the cytoplasm of macrophages with some staining also present in a follicular dendritic pattern. Two color immunohistochemical analysis of tissue with anti-p24 (brown) and anti-fes (red) indicates the presence of dual colored cells (orange) expressing both p24 (from HIV) and c-fes/fps (activated by being positioned downstream of the HIV integration site). Macrophages were isolated from the GH AILD spleen by adherence, and the cells were dual stained with anti-Fes and anti-p24. Orange macrophages were observed showing that Fes and p24 co-localize in macrophages. Therefore, although no clonal form of T-cell or B-cell was present in the GH AILD, the finding of a clonal form of HIV and p24 expressed intracellularly with the AILD-associated macrophages suggests that the, clonal form of HIV resides in a clonal macrophage-like cell. In the cases shown in Table I where frozen specimens were available, intense Fes staining was predominantly associated with macrophage-like cells as was p24 staining. One case however, showed intense Fes staining without p24 staining but had an abundance of clonal HIV integrated near (in the 3'z exon of fur) the c-fes/fps gene (Case 11). Therefore c-fes/fps expression can be influenced by HIV in the absence of HIV gene expression.

Cytokines are Involved in Macrophace-Associated Lymphomas

Cytokines are normally involved in lymphocytic proliferation. Interleukin-6 (IL-6) is a pleiotropic cytokine produced by various cell types that regulate immune responses, acute phase reactions and hematopoiesis (Akira, S. et al., *Immunol Review* (1992) 127:25–50). Many cell types, including monocyte/macrophages, fibroblasts, endothelia, B and T lymphocytes, chondrocytes, astrocytes and keratinacytes are capable of producing IL-6. IL-6 can exert growth-inducing, growth-inhibitory or differentiation inducing activities depending upon the nature of the target cells. In regard to lymphocytic stimulation IL-6 has been shown to be involved in 1) terminal differentiation of B-cells into antibody producing plasma cells; 2) induction of IL-2 and IL-2 receptors and differentiation of T-cells; and 3) IL-6 has been shown to cause growth of myeloma and hybridoma cells (Woodruff, C., et al., *DNA and Cell Biology* (1992) 11:587–592). IL-6 may cause transformation of IL-6 receptor expressing cells (Tohyama, N., et al., *J ExD Med* (1990) 171:389). IL-6 producing macrophages and endothelial cells were shown to be present in primary cultures of AIDS-associated large cell immunoblastic lymphomas (Emilie, D. et al., *Blood* (1992) 80:498–504), however no association with HIV integration or clonal macrophage expansion was described.

Inhibition of Cytokines In Vitro Blocks Lymphocytic Proliferation

Three patients with large-cell lymphoma malignant ascites were studied for in vitro effects of IL-6 and IL-10 on cell proliferation. The ascites fluid contained high concentrations of IL-6 and IL-10 and neutralizing antibodies to these cytokines blocked lymphoma cell proliferation. This observation is consistent with cytokines such as IL-6 and IL-10 inducing lymphomagenesis in vivo. The presence of a clonally expanded population of macrophages associated with lymphoid tumors suggests that the macrophages, by secreting cytokines, are secondarily inducing surrounding untransformed cells to overgrow, thus causing tumorigenesis.

Identifying Cells Containing the Inteqrated HIV and Expressing Cytokine

Because many of the lymphomas that contain clonally integrated HIV represent mixed immunophenotype lymphomas that contain B-cells, T-cells, and prominent macrophages, it is important to determine which cell type contains the clonal. form of HIV. As described in Table I above, multiple disease categories were described wherein HIV was found to be clonally integrated. These include mycosis fungoides, cutaneous T-cell lymphoma, systemic T-cell lymphoma, mixed immunophenotype/polyclonal lymphoma, AILD and Hodgkin's disease. The same procedure is useful in analyzing various categories of lymphoma found to have integrated forms of HIV wherein cell subpopulations can be analyzed (by cell sorting or dual staining, for example) to identify the cell type containing the clonal HIV.

RFLP Analysis of Non-HIV Macrophages for Clonality

In the event that macrophage-rich cancerous tissue is found to lack HIV, the clonality of the cell population (e.g., the macrophage population) is determined as above by first sorting the cells into subpopulations according to cell surface marker reactivity. The macrophage or other cellular subpopulation is tested for clonality by RFLP analysis well known to those skilled in the art. RFLP analysis according to the invention involves probing the restriction digested and gel separated DNA with nucleic acid probes that hybridize to specific mammalian (preferably, human) genomic DNA regions.

The genomic regions of interest include, but are not limited to, regions which flank common viral (e.g., HIV) integration sites associated with cellular transformation such as sites near genes associated with the control of cell proliferation (e.g., an oncogene). The fur gene Z exon shown herein to be the site of HIV integration associated with clonal macrophage expansion is an example of a genetic region to which nucleic acid probes can be hybridized for determining clonality by RFLP analysis using the diagnostic method of the invention. It is well known in the art of molecular and cellular biology that genetic mutations or rearrangements can occur causing the abnormal expression of a particular gene such as an oncogene. Thus the integration of HIV or other virus is not required for abnormal expression of a gene adjacent to a frequently observed site of integration.

Treatment of Lymphoma Containing HIV-Integrated Macrophages

SCID mice are injected with human splenic tissue containing clonal HIV-integrated macrophages (e.g., tissue from Case 10). Control SCID mice are injected with normal (no HIV association, non-cancerous) splenic tissue. Growth of tumors in the control and test mice are monitored; the rate of growth of the HIV-associated tumor exceeds that of the control.

To illustrate the ability of a macrophage-targeted cytotoxic agent to inhibit the growth of macrophage-induced cancerous tissue, the following example is described. SCID mice harboring HIV-integrated macrophage-induced cancerous tissue (as described above) are divided into control and test groups. To test group 1 is administered a cytotoxic agent in a formulation that delivers the cytotoxic agent preferentially to the macrophages by the method of the invention (e.g., liposome encapsulated cytotoxin). To control group 1 is administered a formulation identical to that given to the test group but without the cytotoxic agent. Tumor growth in test group 1 is compared to tumor growth in the control group 1.

Complementary treatment of the non-macrophage tumorous tissue further inhibits tumor growth. To test group 2 is administered the macrophage-targeted cytotoxic agent in a formulation as described above. To test group 2 is administered a second cytotoxic agent preferentially targeted to cancerous tissue (e.g., rapidly growing cells). To control group 2 is administered only the second cytotoxic agent formulation targeted to cancerous tissue. The tumor growth in test group 2 is compared to test group 1 as well as the controls to determine the effectiveness of complementary treatment of the surrounding tissue while also treating the growth-inducing macrophages. Growth inhibition of both the clonally expanded macrophages and the surrounding tissue in complementary treatments further decreases the size of the tumor.

Pathogenic Model of Lymphomagenesis

The discovery of the invention is that HIV may play a direct role in the step-wise development of lymphoma in HIV disease. Clonal HIV-infected macrophages were present at a high frequency in polyclonal lymphoma and polyclonal AILD wherein no clonal B- or T-cell markers were observed. In a separate measurement of clonality (i.e. IPCR for mapping clonal forms of HIV) we have found HIV to be frequently present in a clonal form within these types of tumors. We have shown that in the cases examined, this clonal HIV was present within tumor-associated macrophages and thus, can be contributing to the polyclonal proliferation of lymphoma and angioproliferation of AILD through secretion of cytokines typically secreted by macrophages. The common integration site within 6 of 13 separate tumors indicated a role for c-fes/fps in the process of macrophage-induced tumorigenesis. At least 5% of the cells within these tumors bears a clonal form of HIV, and the only cells found expressing HIV have been cells of the macrophage lineage except for the previously studied case where HIV was present in the malignant T-cells. Therefore we propose a model that a slow expansion of clonally infected macrophage-like cells represents an early stage in lymphomagenesis, and because of overstimulation of the lymphoid element with macrophage secreted cytokines (e.g., IL-6), leads to the development of polyclonal and subsequently monoclonal lymphomas.

Clonality isolated to one tissue type (e.g., macrophage) is indicative of early stage macrophage-induced tumorigenesis. Later stages are likely to contain clonal populations of other cell types as growth stimulation leads to outgrowth of some clones.

The development of clonal lymphoid lymphoma can also occur in hyperproliferative tissue through events such as chromosomal translocation where the chromosomal translocation within a clonal population of macrophages causes expression of an oncogene or overexpression of cytokines leading to tumorigenesis in the surrounding tissue.

The pathogenesis of Hodgkin's disease wherein the Reed-Sternberg cell is thought to contribute to gross tumor development through the expression of cytokines such as IL-6 parallels the. clonal HIV-containing macrophage-induced lymphomas described above in that c-fes/fps is expressed uniformly in Reed-Sternberg cells in non-AIDS-associated Hodgkin's disease (Trumper, L. H. et al., *Blood* (1993) 81:3097–3115).

Experimental data: Materials and Methods

Detecting Clonally Integrated HIV-1 by IPCR

Using IPCR (inverse polymerase chain reaction), lymphomas from HIV-infected individuals were identified containing clonally integrated HIV-1.

DNA was extracted from fresh or frozen tissue by standard techniques as previously described (Maniatis, T., et al., *Molecular Cloning: A laboratory manual* (1982) Cold Spring Harbor Laboratory, Cold Spring Harbor, N.Y.). DNA from fixed paraffin-embedded tissue can be prepared for example by placing thin sections of the tissue in an Eppendorf tube and removing :the paraffin with xylene. After rinsing with ethanol, the sample was digested with proteinase K (0.5 mg/ml) and 1% SDS at 500° C. for 24 hours in TEN buffer (100 Mm Tris-Cl, 40 Nm EDTA, 10 Mm NaCl, Ph 8). The concentration of proteinase K and SDS are then adjusted to 1 mg/ml and 1%, respectively, and continue incubating for another 24 hours. Following phenol and chloroform:isoamyl alcohol extraction, the DNA is precipitated with sodium acetate and ethanol and dried.

IPCR was performed on DNA isolated from fresh, frozen and fixed tissue as described above or by equivalent techniques known to those skilled in the art. The procedure was performed as described by Shiramizu et al. (Shiramizu, B. et al., (1994), suora). DNA (0.1 μg) was digested with Sau3A (or other frequent cutter) and ligated in a 200 μl reaction: 1X ligase buffer (NEB, Beverly, Mass.), 40U T4 DNA ligase (NEB) for 36 hours at 15° C., a DNA concentration favoring self-ligation of the DNA fragments to form circles. The reaction was purified by ethanol precipitation and followed by IPCR (FIG. 1): 100 Pm primers (CWLB and CW2H, FIG. 1), 1 μl ligated product, 1X Taql DNA polymerase buffer, 20 Nm dNTP's, 2.5 U Taql DNA polymerase (Promega Biotech, Madison, Wis.) in a Cetus-Perkin Elmer thermocycler (Cetus-Chiron, Emeryville, Calif.). Conditions: 94° C. melting for 1.5 min, 50° C. annealing for 1.5 min, 720° C. extension for 3 min, for a total of 60 cycles. Amplified products were separated on an ethidium-stained gel (1–2% agarose/1–2% NuSieve gel, FMC BioProducts, Rockland, Me.). To verify the amplified products, the DNA from the agarose gel was transferred to a nylon membrane and prepared for hybridization by standard techniques (Maniatis, T. et al., (1982) supra). The nucleic acid probes used for hybridization were LTRP, Furl, and Fur2 (FIG. 1). The probes were labeled with digoxigenin and detected by chemiluminescence (Boehrenger-Mannheim, Germany) or labeled by other standard techniques (e.g., radiolabel, biotinylation, fluorescence label).

To identify the cells containing the clonal HIV, the cell population is sorted as described above and the DNA isolated from each cell type is analyzed by IPCR. Alternatively, the DNA isolated from the mixed cell population is analyzed by IPCR followed by dual staining of tissue to localize an HIV product such as p-24 in a particular cell type. In situ hybridization techniques are also standard in the art for the localization of specific sequences (such as HIV) in the event that the integrated HIV sequences are inactivated and do not produce identifiable proteins. Dual staining using anti-CD14 antibody and anti-p24 antibody would identify the dual stained cell as a macrophage containing HIV. Antibody staining is well known in the art; antibodies used for staining may be pre-labeled (covalently attached to a detectable marker) or labeled following attachment to the protein of interest (such as a biotin-IgG/streptavidin system well known in the art). The previously determined clonality of the HIV sequences indicate that the anti-p24 stained macrophage is a member of a clonally expanded population of macrophages associated with the cancerous tissue.

Flow Cytometry Cell Separation

Single cell suspensions from newly diagnosed or cryopreserved lymphomas are prepared by pressing fresh lymphoma tissue through steel mesh screens. If the lymphoma contains a monoclonal HIV by IPCR, the single cell suspensions will be stained with monoclonal antibodies as previously described (Mercolino, T. J. et al., *CD5 B cells in development and disease* (1992) L. Herzenberg, K. Rawjesky and G. Haughton, eds., (New York Academy of Sciences) 409–421). Useful antibodies include: anti-CD14 which will identify macrophages; anti-CD4 which will identify CD4+ T-cells as well as macrophages; anti-CD8, anti-CD20 which identifies B-cells, anti-CD-30 (Ki-1); and anti-CD15 which identifies Reed-Sternberg cells. The cells are sorted using a FACS Vantage cell sorter or equivalent that has been equipped with a biohazard containment compartment capable of sorting live cell suspensions from HIV-infected specimens. Macrophages may be individually sorted from the other cells in a mixed population by initially tagging with a macrophage specific cell surface antibody such as labeled anti-CD14 followed by cell sorting and collecting anti-CD14 tagged cells separate from all other cells. The sorted cell specimens are subjected to IPCR as described above. Cytocentrifuge preparations from the sorted cells is stained with anti-HIV p24 antibodies by standard techniques to determine whether the cells containing clonally integrated HIV also express HIV structural determinants. Sorted cell populations are also useful for performing RT-PCR (reverse transcriptase polymerase chain reaction) to determine the spectrum of cytokines expressed by each population of cells. Alternatively, macrophages may be separated from other cell types in a mixed population by adherence to glass or plastic (such as glass or plastic beads or the sides of a glass or plastic container). Non-adhering cells are removed and retained for separate analysis as necessary.

Double-Staininc Immunocytochemistry

A standard immunoperoxidase protocol well known in the art is used with slight modifications for double-antibody detection (Herndier, B. G. et al., AIDS (1994) 8:575–581. The p24 antibody (DAKO, Carpinteria, Calif.) is used for HIV localization. C-fes antibody was prepared from a hybridoma culture obtained from American Type Culture Collection (HB8595) (Gaithersburg, Md.).

The fixed-tissue slides were hydrated in graded ethanol with a final wash in distilled water. The slides were then blocked and buffered with 0.5% Casein in phosphate buffered saline (PBS) for 30 minutes. The p24 antibody was incubated on the slide for I hour at room temperature. The slide was then washed in Casein-PBS for 5 minutes. The slide was then incubated with biotin-conjugated anti-mouse IgG for 30 minutes at room temperature. The slide was washed in Casein-PBS for 5 minutes, followed by diaminobenzidine incubation for 7–10 minutes. After washing in distilled water, an incubation with 0.5% $CuSO_4$ for 5 minutes was performed and washed with water for 2 minutes. The slide was then incubated for 10 minutes in 1N Hcl, followed by a wash with water and incubation in Casein-PBS for 15 minutes. The slide was then incubated with anti-fes or anti-p24 antibody for 1 hour at room temperature, followed by a. Casein-PBS wash. The slide was then incubated with biotin-conjugated IgG at room temperature (anti-mouse IgG made in horse; BioGenex, San Ramon, Calif.) for 30 minutes. After washing in Casein-PBS for 5 minutes, the slide was incubated with alkaline-phosphatase-conjugated streptavidin (BioGenex) at room temperature for 30 minutes. Following a wash in Casein-PBS for 5 minutes, the slide was then incubated with Vector Red Alkaline Phosphatase Substrate Kit I (Vector Lab) for 10–15 minutes, .washed in water for 2 minutes and counterstained with Hematoxylin for 1 minute. The-slide were washed in water for 1 minute followed by a wash of diluted ammonia in water, then followed by a wash of graded ethanol and xylene. This method was also useful for p-24 staining. Means for detecting antibodies are well known in the art; the above procedure provides an example.

Identifying c-fes/fps-Expressing Cells

To identify cells expressing c-fes/fps within tumors found to have HIV clonally integrated upstream of c-fes/fps, two color immunofluorescence studies were performed as described above on fixed and permeablized cells. Antibodies described above for identifying cell type are used in a first immunostaining followed by a fixation and permeablization with Ortho permafix (Ortho Pharmaceuticals, Raritan, N.J.) (or equivalent) that will allow staining of intracellular Fes protein with an anti-fes-oncogene-antibody (ATCC HB8595). These two-color studies are performed on tumor tissue as well as control lymph node tissue as there is a small amount of Fes expressed in normal macrophages. An activated form of a Fes-specific rabbit anti-sera can also be prepared by standard techniques as a useful stain since normal macrophages do not express the activated form of Fes. The first stage antibodies are directly conjugated to FITC, whereas the second anti-fes antibodies have a phycoerythrin-labelled second stage antibody.

Cytokine and Cell Proliferation Gene Expression

Cytokine and cell proliferation gene expression is monitored by the following standard technique. Cellular RNA is extracted from sorted cell populations as previously described (Chomzynsky, P. and Sacchi N., *Anal Biochem* (1987) 162:145). Moloney leukemia virus reverse transcriptase is used to reverse transcribe cellular RNA into CDNA. RT-PCR utilizing cytokine primers designed to hybridize with the CDNA of known cytokines is performed on the CDNA as previously described (Trumper, L. H. et al., (1993) supra; Brenner, Ca et al., Biotechnioues (1989) 7:106). Useful primers include but are not limited to primers for Interleukins 1–13, c-fes/fps oncogene, basic fibroblast growth factor, TNF-α (tumor necrosis factor-α), and GMCSF (granulocyte macrophage colony stimulating factor). Primers are easily designed and synthesized by one skilled in the art since the sequences of the relevant genes are known and synthetic techniques are routine.

Use

The invention is used for the early detection and diagnosis of clonally expanded macrophages in pre-cancerous or cancerous tissue. Clonality in macrophages indicates an early stage of lymphoma induced by clonal macrophages since later stages often contain clonal populations of the surrounding tissue as well. Thus the diagnostic method and kit of the invention are useful in diagnosing the involvement of HIV in a given tumor; diagnosing the involvement of clonally expanded macrophages inducing the growth of surrounding tissue; indicating the stage of tumorous growth so as to aid in the evaluation of a patient's disease; and providing information about the nature of the pre-cancerous or cancerous tissue such that alternative treatment may be followed if indicated.

The treatment method of the invention is useful in targeting the growth stimulating macrophages determined to be associated with the tumor by the diagnostic method of the invention. By inhibiting or ablating the cytokine-producing macrophages associated with the tumor, the growth of the surrounding tissue is substantially blocked. The treatment method of the invention is useful by further providing for the complementary treatment of macrophages as well as the growth-induced surrounding tissue leading to a complete treatment of the mixed immunophenotype lymphoma or other cancerous tissue.

The invention is useful in diagnosing and treating several diseases associated with primary clonal expansion of a cell type (such as a macrophage or follicular dendritic cell) which induces a secondary cell to proliferate. Disease that can be diagnosed and treated by the invention are listed, without limitation, in Table II, column 1. The cell type (primary cell) which expands initially (through HIV insertion or genetic alteration resulting in expansion) and which induces other cells to proliferate is presented in column 2. The cells (secondary cells) which respond to the inducing signals and proliferate are presented in column 3. The invention is also useful in diagnosis and treating other diseases in which clonally expanded inducer cells promote proliferation of responder cells in early stages of a cancer as shown, without limitation, in Table II.

TABLE II

Summary of Diseases That Can be Diagnosed and Treated by the Invention

| Disease | Primary Transformed Cell ("Inducer") | Secondary Transformed Cell ("Responder") |
|---|---|---|
| Mucosal-associated lymphoid tumors | Follicular dendritic cell (lamina propria germinal cell) | B-cell |
| Follicular lymphoma | Follicular dendritic cell | B-cell |
| Autoimmune lymphomas | Defective retroviral infected macrophage (i.e., Sjögren's virus) | B or T-cell |
| Mycosis Fungoides | Langerhans cells | T-cell |
| Ki-1 positive anaplastic T-cell | Macrophage | T-cell |
| Kaposi's Sarcoma | Bowel macrophage | Endothelial cell |
| Multiple myeloma | Bone marrow stroma | Plasma cell |
| AILD - B-cell | Defective follicular dendritic cell | B-cell |
| AILD - T-cell | | T-cell Endothelial cell |
| Polyclonal B-cell | Defective follicular dendritic cell | B-cell EBV-infected B-cell |
| Hodgkin's Disease | Reed-Sternberg cell | lymphocytes and fibroblasts |
| Breast Cancer | Macrophage | Ductal cells and fibroblasts |

Other embodiments are within the following claims.

What is claimed is:

1. An isolated macrophage of a mammal having integrated into its genome a retroviral transcriptional controlling sequence positioned relative to a cell proliferation gene such that the presence of said retroviral transcriptional controlling sequence and said cell proliferation gene results in macrophage proliferation.

2. The macrophage of claim 1, wherein said retroviral transcriptional controlling sequence is a functional promoter sequence that increases expression of said cell proliferation gene.

3. The macrophage of claim 1, wherein said retroviral transcriptional controlling sequence is a functional enhancer sequence that increases expression of said cell proliferation gene.

4. The macrophage of claim 1, wherein said cell proliferation gene is an oncogene.

5. The macrophage of claim 4, wherein said oncogene is selected from the group comprising c-fes/fps, c-myc, and ras.

6. The macrophage of claim 1, wherein said transcriptional controlling sequence is an enhancer/promoter sequence in an LTR of a human immunodeficiency virus.

7. A method of screening for an agent that reduces macrophage viability, said method comprising contacting said macrophage of claim 1 in vitro with a candidate agent; and determining the effect of said candidate agent on said macrophage.

8. A method of screening for an agent that reduces macrophage viability, said method comprising implanting into a non-human mammal a tumor tissue comprising a macrophage having integrated into its genome a retroviral transcriptional controlling sequence positioned relative to a cell proliferation gene such that the presence of said retroviral transcriptional controlling sequence and said cell proliferation gene results in macrophage proliferation;

administering a candidate agent to said mammal; and determining the effect, if any, of said candidate agent on viability of said macrophage.

9. A method of screening for an agent that reduces macrophage viability in a non-human mammalian host, said method comprising contacting a macrophage with a candidate agent in said host, wherein said macrophage has integrated into its genome a retroviral transcriptional controlling sequence positioned relative to a cell proliferating gene such that the presence of said retroviral transcriptional controlling sequence and said cell proliferation gene results in macrophage proliferation, and wherein said host has a tumor comprising said macrophage; and determining the effect of said candidate agent on said macrophage.

10. The method of claim 9, wherein said mammal is a mouse.

11. The method of claim 9, wherein said tumor is in a tissue of said mammal selected from the group consisting of skin, peritoneum, and spleen.

12. The method of claim 9, wherein the effect of said candidate angent on said tumor is determined.

* * * * *